United States Patent
Natarelli

(10) Patent No.: US 11,051,459 B2
(45) Date of Patent: Jul. 6, 2021

(54) APPARATUS TO PROVIDE MAXIMUM PPFD LIGHT RECIPES TO HORTICULTURAL LIGHTING

(71) Applicant: David John Natarelli, Ionia, NY (US)

(72) Inventor: David John Natarelli, Ionia, NY (US)

(*) Notice: Subject to any disclaimer, the term of this patent is extended or adjusted under 35 U.S.C. 154(b) by 231 days.

(21) Appl. No.: 16/270,188

(22) Filed: Feb. 7, 2019

(65) Prior Publication Data

US 2020/0253128 A1    Aug. 13, 2020

Related U.S. Application Data

(60) Provisional application No. 62/634,841, filed on Feb. 24, 2018.

(51) Int. Cl.
*A01G 7/04*    (2006.01)
*A01H 3/02*    (2006.01)
*H05B 45/10*   (2020.01)
*H05B 47/19*   (2020.01)

(52) U.S. Cl.
CPC ............... *A01G 7/045* (2013.01); *A01H 3/02* (2013.01); *H05B 45/10* (2020.01); *H05B 47/19* (2020.01)

(58) Field of Classification Search
CPC .................................. A01G 7/045; A01H 3/02
See application file for complete search history.

(56) References Cited

U.S. PATENT DOCUMENTS

2019/0110406 A1 * 4/2019 Adams .................... F21V 5/007

FOREIGN PATENT DOCUMENTS

| KR | 20140049260 A | * | 4/2014 | ............ H05B 45/37 |
| WO | WO-2010078630 A1 | * | 7/2010 | ............ H05B 45/37 |
| WO | WO-2015154798 A1 | * | 10/2015 | ............ A01G 9/26 |

* cited by examiner

*Primary Examiner* — Charlie Y Peng
(74) *Attorney, Agent, or Firm* — Chen-Chi Lin

(57) ABSTRACT

A control device for horticultural lighting applications which allow for the creation of nearly unlimited color selection while maintaining constant power output across the multiple LED light engines connected to it.

13 Claims, 3 Drawing Sheets

APPARATUS TO PROVIDE MAXIMUM PPFD LIGHT RECIPES TO HORTICULTURAL LIGHTING

CROSS REFERENCE TO RELATED APPLICATIONS

This application is intended to claim the benefit of Application No. 62/634,841, filed on Feb. 24, 2018.

TECHNICAL FIELD

This document pertains generally, but not by way of limitation, to horticultural artificial illumination.

BACKGROUND

The transition from high intensity discharge (HID) lighting to light emitting diode (LED) lighting has offered new advantages that have not been available before. One such advantage is the ability to offer many different colors of light. It is a known fact that plants respond differently to specific colors with in the visible light spectrum. To date all LED lighting only offer one specific color within the visible spectrum without the ability to change this. This makes the light only usable for a small group of plants and not all plants. Another problem with the existing LED lighting is that within that specific light color they do not allow maximum power output of the individual colors that make up the specific color. An example of this problem is one light manufacturer may provide a 200 W light that provides 100 W of white light, 50 W of blue light, and 50 W of red light which may be acceptable for a plant at one time in its life cycle, however at a different time in its life cycle it may need red only and not the white or blue and the light may allow you to disconnect the white and blue however the total output power is now reduced from 200 W to 50 W reducing the Photosynthetic Photon Flux Density (PPFD) the plant receives. It is well known in the horticultural industry that maximum PPFD is critical for plant growth.

SUMMARY

The present inventor has recognized, among other things, that a problem to be solved can include providing a light recipe to the plants that may include light from the entire light spectrum that changes over the course of the plant's life cycle. Another problem to be solved is to provide the maximum PPFD of light no matter what the light recipe required is. The present subject matter can help provide solutions to these problems, such as a controller that can accept custom light recipes from various inputs such as, but not limited to, smart phones, the internet, and a computer or tablet and provide maximum PPFD to lighting elements connected to it, in such a way that at all times the maximum allowable power, and thus PPFD, is being supplied to the lighting elements, regardless of the light recipe chosen.

This overview is intended to provide an overview of subject matter of the present patent application. It is not intended to provide an exclusive or exhaustive explanation of the invention. The detailed description is included to provide further information about the present patent application.

DESCRIPTION

Figure 1:
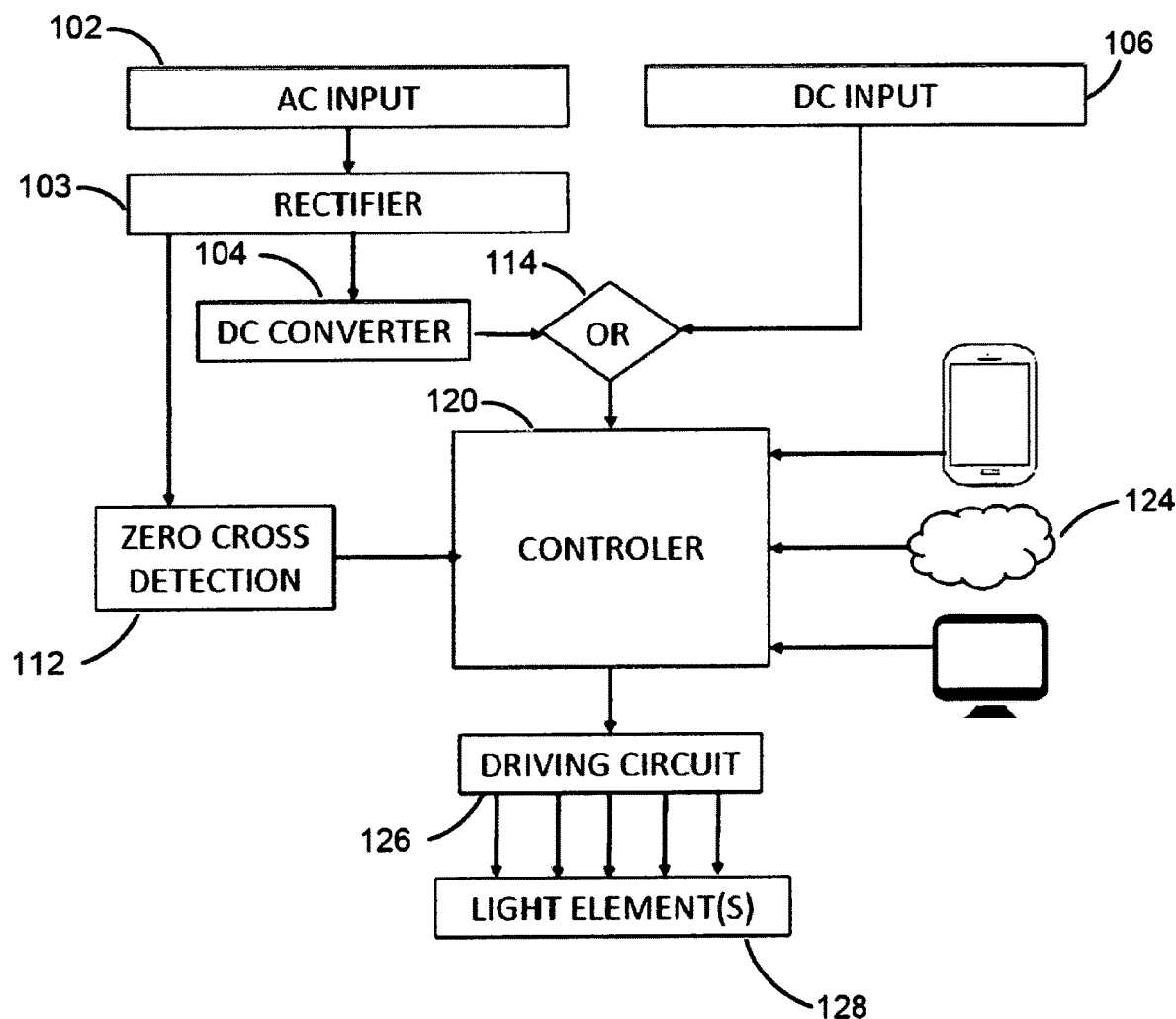
FIG. 1 is a functional block diagram of the complete system.

FIG. 1 depicts a block diagram of a controller circuit 100. Controller circuit 100 receives either an alternating current 102 or direct current 106. The alternating current 102 is a sinusoidal input, such as a 120 volt at 60 Hz nominal input or a 230 volt at 50 Hz nominal input. The direct current 106 is a steady state input, such as 48V. Other voltage and frequency combinations can also be accommodated by techniques described herein. The sinusoidal input of 102 can be rectified by a full-wave rectifier 103 to generate an input with double the nominal frequency that periodically oscillates between zero volts and its nominal voltage. The DC converter 104 establishes the required DC operating voltage for the controller to function, such as 3.3 VDC or other such voltage required by the controller. Zero cross detection circuit 112 provides to the controller with the point in time where the alternating current 102 crosses the 0V point, or a point thereabout, which reoccurs twice the frequency of the input alternating current 102. The OR 114 identifies to the controller 120 if input alternating current 102 or direct current 106 was used to supply controller circuit 100, which is required to determine the required output control to the driving circuit 126.

A sequence of control times and light colors known as a light recipe is provided to the controller 120 by inputs 124. The inputs can come from various wireless means such as but not limited to computer Wi-Fi and Bluetooth phone app, and most importantly files stored on a website over the internet. Once the light recipe is received it is stored on the controller and used to control driving circuit 126.

During operating controller 120 uses the input light recipe 124 along with zero cross detection 112, if alternating current 102 is used to supply the control circuit 100, to determine the required output signal to driving circuit 126 which provides constant power to lighting element(s) 128 throughout the light recipe sequence. The power from driving circuit 126 is applied to lighting element(s) through one or more driving circuit channels, that are connected to one or more light elements, such as LEDs but not limited to LEDs. Lighting element(s) 128 are limited in the amount of power they can receive from driving circuit 126 such that the added power of each channel of light element(s) 128 does not exceed the total allowable power of driving circuit 126. In one example driving circuit 126 is rated at 200 W maximum power that can be dissipated, while each of 4 the channels of different color lighting element(s) can independently handle 200 W thus allowing at any given time one color to be operating at the maximum allowable power but alternatively it is not possible for all of the color channels to be operating at their maximum allowable power at the same time because if so the combined color lighting element(s) would have to dissipate 800 W, thus destroying driving circuit 126. Controller 120 is responsible for scaling light recipes received from input 124 such that it maximizes the power dissipation to each channel, maintains the correct ratio of power to each channel, and does not exceed the maximum power dissipation of driving circuit 126.

By providing accurately timed pulses to the driving circuit 126, the individual lighting element(s) 128 can be operated in such a way as to make sure the maximum amount of power is always being delivered to the combined individual lighting element(s) 128, unless the light recipe calls for power less than the maximum.

Figure 2:
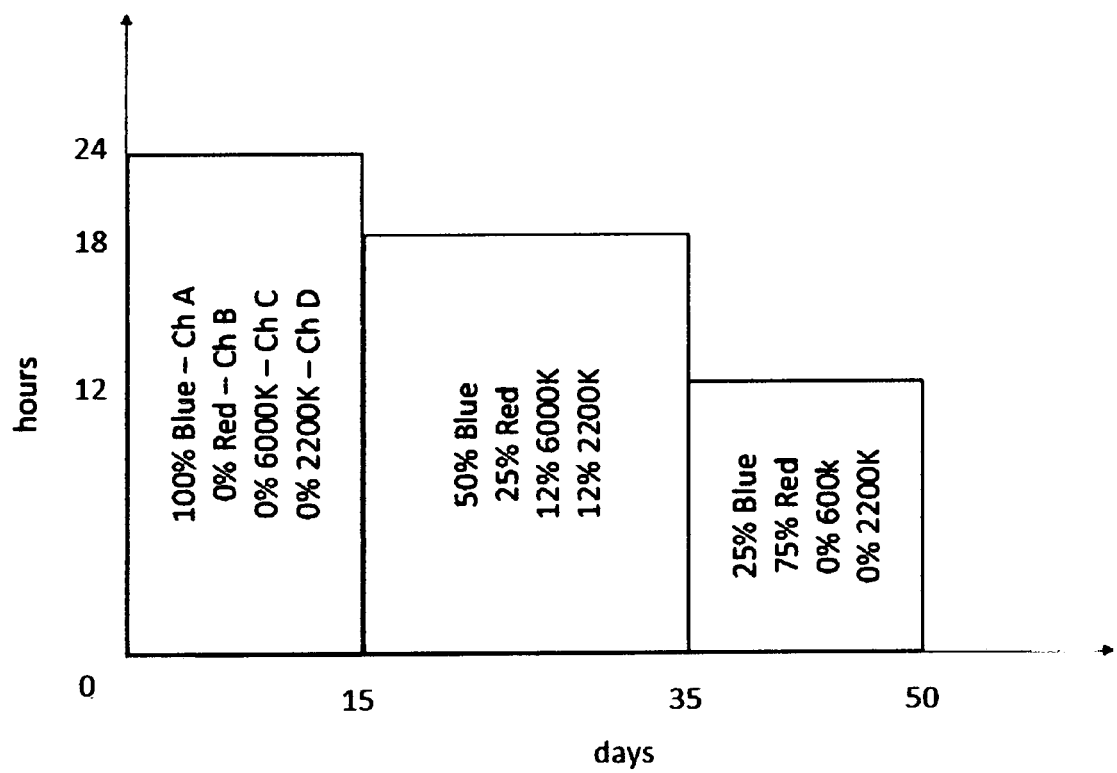
FIG. 2 is an example of a plant light recipe as part of a plant lighting schedule.

FIG. 2 depicts an example bar chart of sample light recipe 200 with the vertical axis representing the hours in one day and the horizontal axis representing the days in one year. Time and day sequence block 201 represents one such sequence block which can be any such sequence block which define the times of the day at which the individual circuit of lighting element(s) 128 of FIG. 1 are operated and for how many consecutive days they are operated at prescribed light outputs. In the sample light recipe 200 sequence block 201 shows that the lighting element(s) 128 of FIG. 1 should be operated for 24 hours each day for a period of 15 days and during this period the outputs of lighting element(s) 128 of FIG. 1 should consist of a first channel, labeled Blue—Ch A being operated at 100% of its possible output, a second channel, labeled Red—Ch B being operated at 0% of its possible output, a third channel, labeled 6000K—Ch C being operated at 0% of its possible output, and a fourth channel, labeled 2200K—Ch D being operated at 0% of its possible output. The output channels of lighting element(s) 128 of FIG. 1 describe here within represent one such possibility and it understood that any amount of output channels can be realized.

FIG. 2 also illustrates example time and day sequence block 202 which shows that the lighting element(s) 128 of FIG. 1 should be operated for 18 hours each day for a period of 20 days and during this period the outputs of lighting element(s) 128 of FIG. 1 should consist of a first channel, labeled Blue—Ch A being operated at 50% of its possible output, a second channel, labeled Red—Ch B being operated at 25% of its possible output, a third channel, labeled 6000K—Ch C being operated at 12% of its possible output, and a fourth channel, labeled 2200K—Ch D being operated at 12% of its possible output.

FIG. 2 also illustrates example time and day sequence block 203 which shows that the lighting element(s) 128 of FIG. 1 should be operated for 12 hours each day for a period of 20 days and during this period the outputs of lighting element(s) 128 of FIG. 1 should consist of a first channel, labeled Blue—Ch A being operated at 25% of its possible output, a second channel, labeled Red—Ch B being operated at 75% of its possible output, a third channel, labeled 6000K—Ch C being operated at 0% of its possible output, and a fourth channel, labeled 2200K—Ch D being operated at 0% of its possible output.

It should be evident that any possible combination of hours, days and power to each channel can be configured in a sample light recipe over the course of a year, but not limited to a year.

Figure 3:
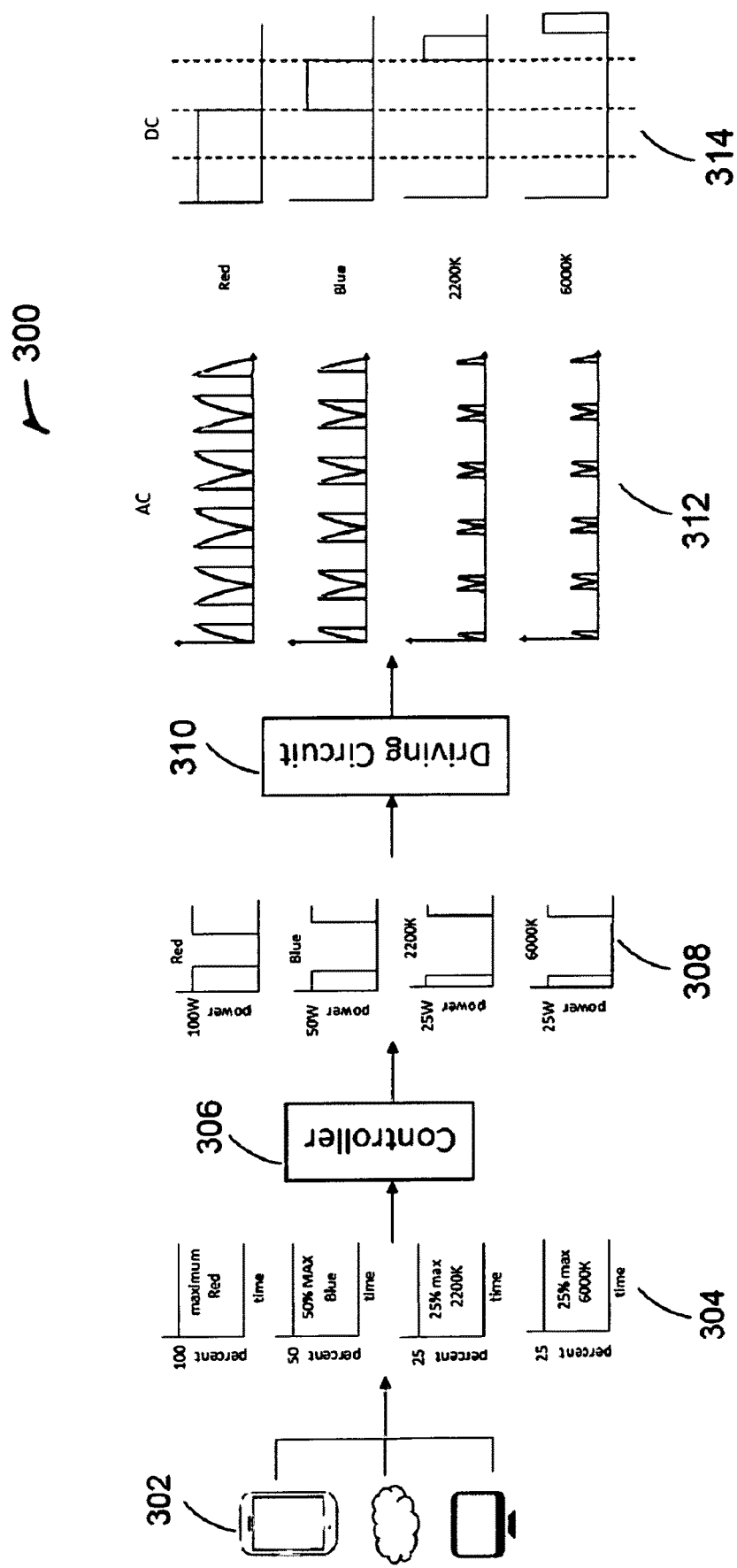
FIG. 3 is an overview of the process or receiving the light recipe from wireless sources and converting it into electrical signals that control the corresponding LED light engines in response to the received light recipe.

FIG. 3 depicts an example timing diagram where 4 signals 308 are applied to driving circuit 310, which drives 4 channels of lighting element(s) 128 of FIG. 1, in response to inputted light recipes 304, where the total allowable power dissipation of lighting element(s) 128 of FIG. 1 is limited to 200 W. In this example each of the 4 driver circuit channels of driving circuit 310 can deliver 200 W of power equaling 800 w of total power than can be delivered to lighting element(s) 128 of FIG. 1, effectively destroying lighting element(s) 128 of FIG. 1 if allowed to deliver its full power.

Light recipe 304 is received by any method of input 302 and supplied to controller 306. Controller 306 level shifts while maintaining the ratio of input values to make sure they do not go over the maximum value that can be delivered to lighting element(s) 128 of FIG. 1. In this example the light recipe 304 received by controller 306 shows that Ch—A is 100% or 200 W, Ch—B is 50% or 100 W, Ch—C is 25% or 50 W, and Ch—D is 25% or 50 W and the output level shifted constant ratio light recipe 308 of controller 306 is such that Ch—A is reduced to 50% or 100 W, Ch—B is reduced to 25% or 50 W, Ch—C is reduced to 25 W, and Ch—D is reduced to 25 W, thus maintaining the same lighting ratio while limiting the power being delivered to lighting element(s) 128 of FIG. 1 to its maximum value of 200 W.

The new Level shifted constant ratio light recipe 308 is received by driving circuit 310 and outputs signals for both alternating current connected lighting elements or direct current connected lighting elements which allow each channel to operate at its maximum power while remaining at or under the maximum allowable amount of the connected lighting element(s) 128 of FIG. 1.

The alternating voltage output signals 312 are controlled and centered around the peak of the input alternating voltage, based on the new level shifted constant ratio light recipe 308 and the zero-crossing of the input alternating voltage. The direct voltage output signals 314 are controlled around the start of each signal, based on the new level shifted constant ratio light recipe 308 and the required starting point for each channel. In this example the off time of the top or first alternating voltage output signal 312 is required to produce 100 W, which corresponds to the red channel of the new level shifted constant ratio light recipe 308. To achieve this 50% of the centered peak of alternating voltage 312 is removed and supplied to the lighting element(s) 128 of FIG. 1. Furthermore, the off time of the second from the top alternating voltage output signal 312 is required to produce 50 W, which corresponds to the blue channel of the new level shifted constant ratio light recipe 308. To achieve this 75% of the centered peak of alternating voltage 312 is removed and supplied to the lighting element(s) 128 of FIG. 1. Even furthermore, the off time of the third from the top alternating voltage output signal 312 is required to produce 25 W, which corresponds to the 2200K channel of the new level shifted constant ratio light recipe 308. To achieve this 87.5% of the centered peak of alternating voltage 312 is removed and supplied to the lighting element(s) 128 of FIG. 1. Even furthermore, the off time of the fourth from the top alternating voltage output signal 312 is required to produce 25 W, which corresponds to the 6000K channel of the new level shifted constant ratio light recipe 308. To achieve this 87.5% of the centered peak of alternating voltage 312 is removed and supplied to the lighting element(s) 128 of FIG. 1. The combined totals of the output alternating voltage signals 312 equal 200 W, which is the maximum allowable power to the lighting element(s) 128 of FIG. 1.

The direct voltage output signals 314 are controlled based on the new level shifted constant ratio light recipe 308 and the required starting point for that channel. In this example the off time of the top or first direct current output signal 314 is required to produce 100 W, which corresponds to the red channel of the new level shifted constant ratio light recipe 308. To achieve this the direct voltage output signal 314 is off for 50% of its total time and its start time is immediately upon receiving a signal. Furthermore, the off time of the second from the top direct voltage output signal 314 is required to produce 50 W, which corresponds to the blue channel of the new level shifted constant ratio light recipe 308. To achieve this the direct voltage output signal 314 is off for 75% of its total time and its start time occurs after the stop time of the previous channel. Even furthermore, the off time of the third from the top direct voltage output signal 314 is required to produce 25 W, which corresponds to the 2200K channel of the new level shifted constant ratio light recipe 308. To achieve this the direct voltage output signal 314 is off for 87.5% of its total time and its start time occurs after the stop time of the previous channel. Even furthermore, the off time of the fourth from the top direct voltage output signal 314 is required to produce 25 W, which corresponds to the 6000K channel of the new level shifted constant ratio light recipe 308. To achieve this the direct voltage output signal 314 is off for 87.5% of its total time and its start time occurs after the stop time of the previous channel. The combined totals of the output direct voltage signals 312 equal 200 W, which is the maximum allowable power to the lighting element(s) 128 of FIG. 1.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform processes as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The claimed invention is:

1. A non-transitory computer-readable storage medium storing instructions that, when executed by a processor, cause the processor to control a lighting system;
   to receive an input direct voltage;
   to receive a light recipe wirelessly through the internet;
   to determine required off times based on the light recipe and a maintained ratio of light outputs;
   to produce direct voltage signals with varying on portions; and
   to illuminate a plurality of lighting elements that can vary with power in a plurality of individual channels;
   wherein said on portions do not overlap with other direct voltage signal on portion; and
   wherein a total power is maintained constant.

2. The non-transitory computer-readable storage medium of claim 1 further comprising a driving circuit coupled to a controller; wherein a respective maximum allowable power of each of the plurality of lighting elements equals to a maximum allowable power of the driving circuit.

3. A method of controlling a plurality of lighting elements, the method comprising the steps of:
   receiving an input alternating voltage;
   determining zero-crossing of the input alternating voltage;
   receiving a light recipe wirelessly through the internet;
   determining required off times based on the light recipe and a maintained ratio of light outputs;
   producing alternating voltage signals with portions removed centered around peak of the input alternating voltage; and
   illuminating the plurality of lighting elements that can vary with power in a plurality of individual channels;
   wherein a total power is maintained constant.

4. The method of claim 3, wherein each of the plurality of lighting elements is an LED.

5. The method of claim 3, wherein said receiving the light recipe wirelessly through the internet from a mobile phone or a tablet app.

6. The method of claim 3, wherein said receiving the light recipe wirelessly through the internet from a computer.

7. The method of claim 3 further comprising a driving circuit coupled to a controller; wherein a respective maximum allowable power of each of the plurality of lighting elements equals to a maximum allowable power of the driving circuit.

8. A method of controlling a plurality of lighting elements, the method comprising the steps of:
   receiving an input direct voltage;
   receiving a light recipe wirelessly through the internet;
   determining required off times based on the light recipe and a maintained ratio of light outputs;
   producing direct voltage signals with varying on portions;
   wherein said on portions do not overlap with other direct voltage signal on portion; and
   illuminating the plurality of lighting elements that can vary with power in a plurality of individual channels;
   wherein a total power is maintained constant.

9. The method of claim 8, wherein each of the plurality of lighting element is an LED.

10. The method of claim 8, wherein said receiving the light recipe wirelessly through the internet from a mobile phone or a tablet app.

11. The method of claim 8 further comprising a driving circuit coupled to a controller; wherein a respective maximum allowable power of each of the plurality of lighting elements equals to a maximum allowable power of the driving circuit.

12. A dimming device comprising:
- a controller;
- a dimming input coupled to the controller, the dimming input providing a dimming value to the controller;
- a zero-crossing detector coupled to the controller, the zero-crossing detector providing a zero-crossing value to the controller;
- a driving circuit coupled to the controller; and
- at least one lighting element coupled to the driving circuit;
- wherein the zero-crossing detector receives an input alternating voltage;
- wherein the controller determines a pulse-off time based on the dimming value, and the zero-crossing value;
- wherein the driving circuit illuminates the at least one lighting element in response to a pulse-off signal from the controller corresponding to the pulse-off time; and
- wherein a respective maximum allowable power of each of the at least one lighting element equals to a maximum allowable power of the driving circuit.

13. The dimming device of claim 12, wherein each of the at least one lighting element is an LED.

* * * * *